United States Patent
Hara et al.

(10) Patent No.: US 8,024,959 B2
(45) Date of Patent: Sep. 27, 2011

(54) GAS SENSOR AND GAS DETECTION METHOD

(75) Inventors: Toru Hara, Takasaki (JP); Takashi Ishiguro, Takasaki (JP)

(73) Assignee: Taiyo Yuden Co., Ltd., Tokyo (JP)

( * ) Notice: Subject to any disclaimer, the term of this patent is extended or adjusted under 35 U.S.C. 154(b) by 500 days.

(21) Appl. No.: 12/237,370

(22) Filed: Sep. 24, 2008

(65) Prior Publication Data
US 2009/0090169 A1 Apr. 9, 2009

(30) Foreign Application Priority Data

Sep. 28, 2007 (JP) .................................. 2007-256345
Jul. 25, 2008 (JP) .................................. 2008-192882

(51) Int. Cl.
*G01N 7/00* (2006.01)
(52) U.S. Cl. .................................................... 73/31.05
(58) Field of Classification Search .................. None
See application file for complete search history.

(56) References Cited

U.S. PATENT DOCUMENTS

| 5,365,770 | A | * | 11/1994 | Meitzler et al. | .............. 73/24.06 |
| 5,481,110 | A | * | 1/1996 | Krishnaswamy et al. | .... 250/288 |
| 5,776,254 | A | * | 7/1998 | Yuuki et al. | ................... 118/725 |
| 2005/0218398 | A1 | * | 10/2005 | Tran | ............................... 257/14 |

FOREIGN PATENT DOCUMENTS

| JP | 2000-121588 A1 | 4/2000 |
| JP | 2001-305089 A1 | 10/2001 |
| JP | 2004-012193 | 1/2004 |

* cited by examiner

*Primary Examiner* — Hezron E Williams
*Assistant Examiner* — Alex Devito
(74) *Attorney, Agent, or Firm* — Law Office of Katsuhiro Arai

(57) ABSTRACT

A gas sensor contains such a dielectric substance having a domain boundary formed between domains with different polarization directions. When a gaseous molecule is adsorbed to the dielectric substance, a transient current is generated due to displacement of the domain boundary under an applied voltage. The adsorbed gaseous molecule is detected by measuring the transient current.

13 Claims, 6 Drawing Sheets

GAS SENSOR AND GAS DETECTION METHOD

BACKGROUND OF THE INVENTION

1. Field of the Invention

The present invention relates to a gas sensor and a gas detection method for determining a gas concentration, useful in various fields of semiconductor manufacturing, food production/manufacturing/distribution, medical care, etc., and more specifically to improved gas sensor and gas detection method suitable for detecting an extremely small amount of a gas.

2. Description of the Related Art

In a field of manufacturing of semiconductor devices such as LSIs (large scale integrated circuits), several hundred ppb (parts per billion) of an impurity is purposefully added to control a semiconductor characteristic. Therefore, the residual oxygen content of a high-purity gas used in this field has to be at a several ppb level (i.e. 1 to 10 ppb level), 2 digits smaller than the several hundred ppb. However, there are still no gas sensors sensitive to the several ppb level. For this reason, an expensive analysis equipment is used in this field.

In a food-related field, it is expected that if a food putrid odor can be detected at a 10 to 50 ppb level, equal to the human olfaction level, food freshness management can be automatized.

Furthermore, in a medical-related field, it is expected that detection of a metabolite from a sickness person (such as acetone from a diabetic patient, methylmercaptan from a periodontitis patient, a volatile sulfur compound, triethylamine, or ammonia from a liver disease patient, carbon monoxide from an asthma patient, or isoprene from an overcholesterol patient) can contribute to early medical diagnosis. In addition, in a deodorant (antiperspirant) field, application of the high sensitivity detection to self check of body odor is under consideration. These fields require a high detectivity at a 1 to 50 ppb level.

As described above, a gas sensor having a concentration sensitivity at the several ppb level can be used in various fields. Conventional gas sensors include semiconductor type gas sensors and surface acoustic wave type gas sensors. For example, JP-A-2000-121588 discloses a gas sensor having a $WO_3$ thin film doped with $In_2O_3$, $SnO_2$, or $Sb_2O_5$ on a gold electrode. An electrical characteristic of the electrode is measured when trimethylamine comes into contact with the thin film. The tungsten oxide has a high sensitivity to the living thing putrid odor causing substance (trimethylamine), has a perovskite-like crystal structure partly, and further has a dielectric characteristic. JP-A-2001-305089 discloses a gas sensor having a metal oxide semiconductor of tin oxide. The semiconductor is doped with both a pentavalent transition metal and a trivalent transition metal, so that oxygen in the air is stably adsorbed to a surface of the semiconductor.

However, the semiconductor type gas sensor has a low detectivity at 1 ppm level. The surface acoustic wave type gas sensor is not suitable for repetitive operation requiring a concentrated gas. In any case, the gas sensors described in JP-A-2000-121588 and JP-A-2001-305089 cannot achieve the high detectivity at the ppb level.

SUMMARY OF THE INVENTION

To solve at least one of the above problems, an object of one or more embodiments of the present invention is to provide a gas sensor and a gas detection method capable of determining a gas concentration at ppb level.

In view of the above, according to an aspect of the invention, there is provided a gas sensor containing a dielectric substance having a domain boundary formed between domains with different polarization directions. In the gas sensor, when a gaseous molecule is adsorbed to the dielectric substance, a transient current is generated due to displacement of the domain boundary under an applied voltage. The adsorbed gaseous molecule can be detected by measuring the transient current. In a main embodiment, a thin film containing $SrTiO_3$ as a main component is used as the dielectric substance, whereby the gas concentration can be determined at the ppb level. In another embodiment, the gas sensor has a heating unit for heating the dielectric substance.

According to another aspect of the invention, there is provided a gas sensor having an insulative substrate, a heating unit formed on the insulative substrate, capable of generating heat on its surface under an applied voltage, a dielectric thin film formed on the heating unit on the insulative substrate with an insulative film in-between, and an electrode unit formed on the dielectric thin film, having electrodes facing each other at a predetermined distance, capable of applying a voltage for measuring a transient current corresponding to a gas concentration. In a main embodiment, the dielectric thin film comprises a polycrystal containing $SrTiO_3$ as a main component. In another embodiment, the dielectric thin film is heated by the heating unit for a predetermined time before determination of the gas concentration, whereby a gaseous molecule adsorbed to the dielectric thin film is released to refresh the film. In a further embodiment, the electrode unit has interdigitated portions facing each other on the dielectric thin film, and extension portions extend from the interdigitated portions respectively.

A gas detection method according to an embodiment of the invention comprises the steps of applying a voltage to a dielectric thin film, which has a domain boundary formed between domains having different polarization directions in a crystal, and measuring a transient current generated due to displacement of the domain boundary corresponding to the concentration of a gaseous molecule adsorbed to the dielectric thin film, thereby determining the concentration. In a main embodiment, the dielectric thin film comprises a polycrystal containing $SrTiO_3$ as a main component.

Another gas detection method according to an embodiment of the invention utilizes the gas sensor, and comprises a refreshing mode of releasing a gaseous molecule adsorbed to the dielectric substance to refresh the substance, and a measuring mode of detecting a transient current, which is generated when a gaseous molecule is adsorbed to the refreshed dielectric substance. In a main embodiment, the refreshing mode comprises a heating mode of heating the dielectric substance using the heating unit, and a backgating mode of applying a reverse electric field to the dielectric substance heated in the heating mode. The reverse electric field is opposite to an electric field generated in the dielectric substance when the gaseous molecule is adsorbed.

The above and other objects, features, and advantages of the invention will become more apparent from the following detailed description and accompanying drawings.

In at least one embodiment of the invention, there can be provided a gas sensor having a relatively high sensitivity to a gas concentration. Further, there can be provided such a gas detection method that a voltage is applied to a dielectric thin film to displace its domain boundary, and a transient current generated under the voltage based on an adsorbed gas amount is measured to determine a gas concentration.

For purposes of summarizing aspects of the invention and the advantages achieved over the related art, certain objects and advantages of the invention are described in this disclosure. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Further aspects, features and advantages of this invention will become apparent from the detailed description which follows.

BRIEF DESCRIPTION OF THE DRAWINGS

These and other features of this invention will now be described with reference to the drawings of preferred embodiments which are intended to illustrate and not to limit the invention. The drawings are oversimplified for illustrative purposes and are not to scale.

DETAILED DESCRIPTION OF THE INVENTION

A preferred embodiment of the present invention will be described in detail below with reference to Examples.

In the present disclosure where conditions and/or structures are not specified, the skilled artisan in the art can readily provide such conditions and/or structures, in view of the present disclosure, as a matter of routine experimentation. Also, in the present disclosure, the numerical numbers applied in specific embodiments can be modified by a range of at least ±50% in other embodiments, and the ranges applied in embodiments may include or exclude the endpoints.

EXAMPLE 1

Figure 1:
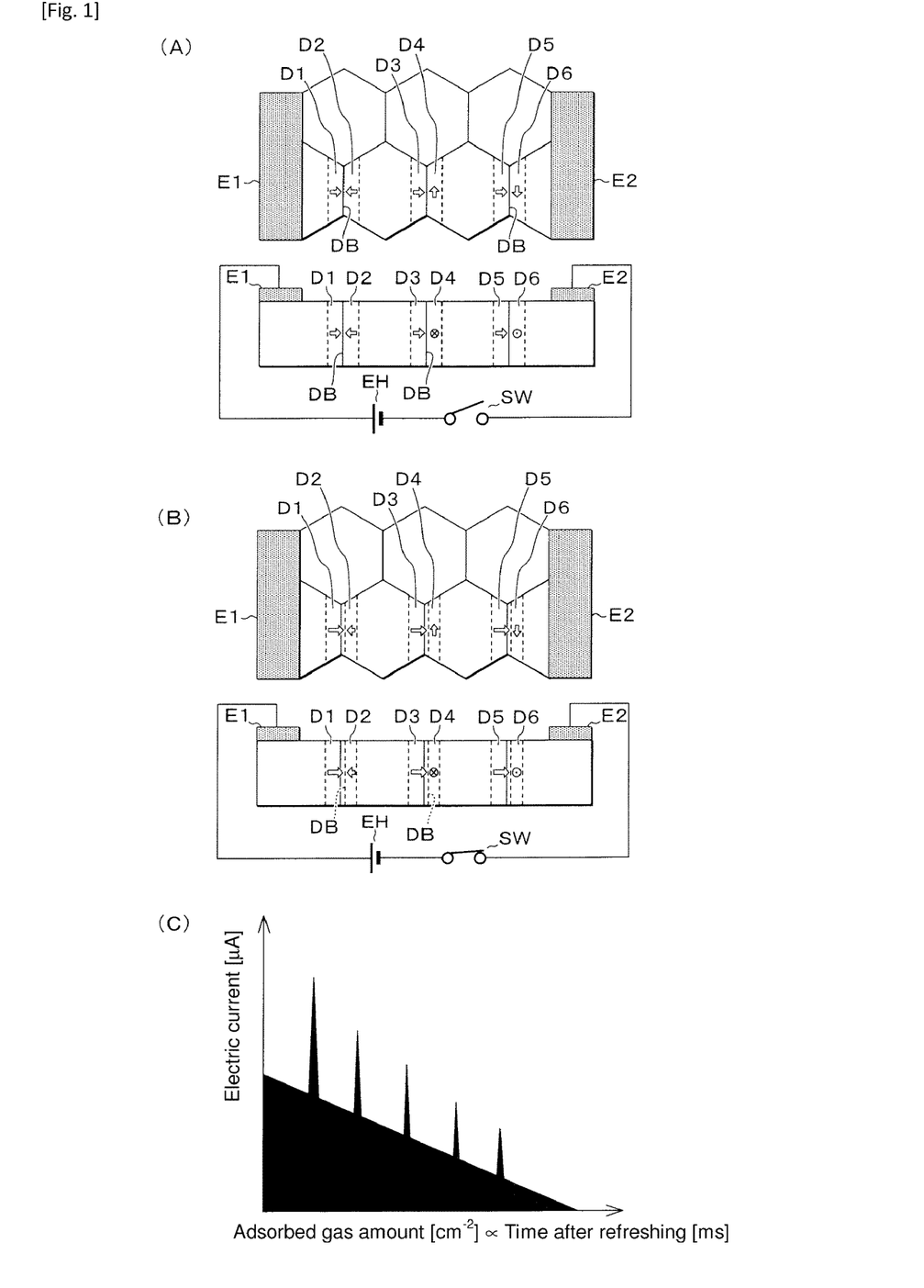
FIGS. 1A to 1C are views showing a basic detection principle of a gas sensor according to an embodiment of the present invention.

First, a basic principle of at least one embodiment of the invention will be described below with reference to FIGS. 1A to 1C and 2A to 2C. The embodiment of the invention utilizes change of a nanodomain structure in a dielectric thin film due to gas adsorption. For example, in a dielectric polycrystal thin film, polarization, electric field, stress, and domain boundary are balanced with each other to minimize the total free energy. An example of the nanodomain structure is partly shown in FIG. 1A. In the nanodomain structure, a grain boundary of a polycrystal is polarized, the polarization directions of domains D1 and D2 are different by 180°, and the polarization directions of domains D3 and D4 are different by 90°. Thus, a domain boundary (a domain wall) DB is formed between domains having different polarization directions, such as the domains D1 and D2, D3 and D4, or D5 and D6. Though the domains on the grain boundaries are shown in FIG. 1A only partly, similar domains are formed on each grain boundary in the polycrystal. In the case of using a single crystal instead of the polycrystal, domains having different polarization properties are formed around a lattice defect, and act in the same manner as in the polycrystal.

When an electron-attracting gas such as an oxygen gas is adsorbed to the polycrystal having this nanodomain structure, the energy balance is deteriorated. At this time, by applying a voltage to the polycrystal, the nanodomain structure is changed, for example as shown in FIG. 1B. Thus, the domain boundary DB between domains, such as the domains D1 and D2, D3 and D4, or D5 and D6, is displaced. As a result, electrons are detrapped from the charged domain boundary DB to generate a high transient current (pulsed current).

A relation between the adsorbed gas amount and the generated current is shown in FIG. 1C. As shown in FIG. 1C, at the start of the gas adsorption, a large number of electrons are trapped in the dielectric thin film, whereby a relatively large trigger current is transiently generated in addition to the original current of the semiconductor. However, as the adsorbed gas amount is increased, the number of the electrons trapped in the dielectric thin film is gradually reduced, and also the electric current is gradually reduced.

Time t [s] required for the gas adsorption can be obtained using the following equation.

$$t = \{1 \times 10^{19} \times (M \times T)^{0.5}\} / \{2.65 \times 10^{24} \times P\}$$

In the equation, P is pressure [Pa], M is molecular weight of a gas, and T is temperature [K]. For example, in the case of using the oxygen gas under conditions of $P_{O2}=1$ [ppb], $M_{O2}=32$, and T=300 [K], the adsorption time is 3.7 [s].

Figure 2:
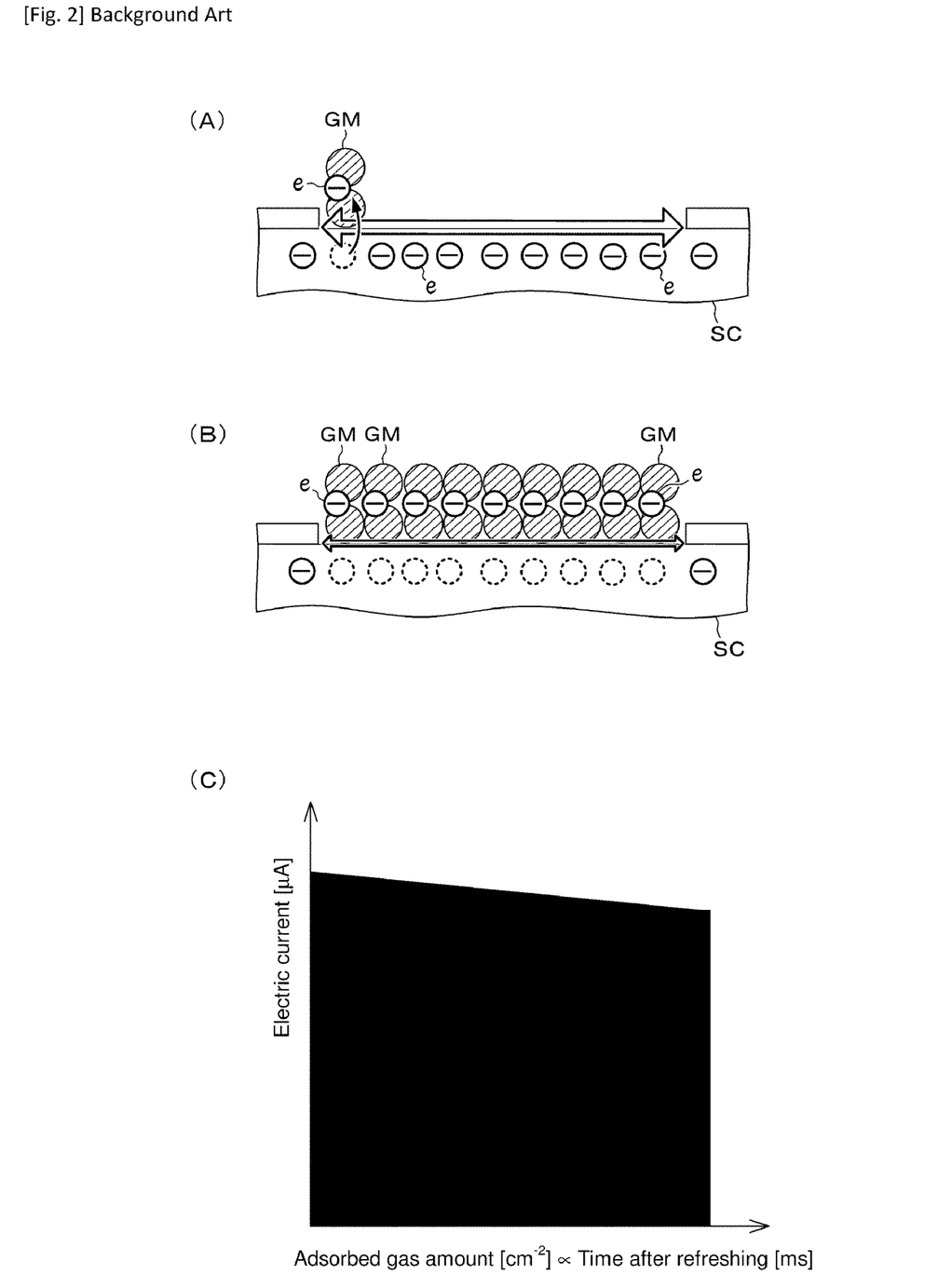
FIGS. 2A to 2C are views showing a basic detection principle of a conventional semiconductor type gas sensor.

On the other hand, in a conventional semiconductor type gas sensor, as shown in FIGS. 2A and 2B, when a gaseous molecule GM is adsorbed onto a surface of a semiconductor SC, an electron e in the semiconductor SC is trapped on the gaseous molecule GM. When only a small amount of the gaseous molecules GM is adsorbed as shown in FIG. 2A, the semiconductor SC contains a large amount of electrons and has a low resistance. However, when a large amount of the gaseous molecules GM are adsorbed as shown in FIG. 2B, the electrons in the semiconductor SC are reduced to increase the resistance. In such a semiconductor type gas sensor, the generated current is gradually lowered with the increase of the adsorbed gas amount as shown in FIG. 2C.

In the case of using a high concentration gas, a detection part of the sensor is covered with the gaseous molecules in a short time. Thus, the resistance of the semiconductor SC rapidly reaches the steady-state value in a short time. On the other hand, in the case of using a low concentration gas, the detection part of the sensor is covered with the gaseous molecules over a long time. Thus, the resistance of the semiconductor SC slowly reaches the steady-state value in a long time. However, in the semiconductor type gas sensor, the transient resistance change is small, and it is difficult to detect the transient response. In contrast, in at least one embodiment of the invention, electrons trapped in a deep energy level in the domain boundary are released to generate a high transient current in addition to a semiconductor-like response. Thus, the transient response can be easily detected, and the gas can be detected at a ppb level.

A dielectric material, preferably used for the dielectric thin film in at least one embodiment of the invention, needs to have many charged domain boundaries. Specifically, it is important that the dielectric material contains a domain not having a polarization direction of 180°. The number of traps for gas adsorption may be effectively increased by introducing a donor or an acceptor. Further, it is necessary that a domain boundary in the dielectric material is displaced by the gas adsorption. Specifically, it is important that the dielectric thin film has a thickness equal to that of an electron depletion layer, a site to be strongly bonded to the gas is exist, and an A site defect at an appropriate density is exist. Furthermore, it is necessary that, when the electric field application is completed, the polarization is rearranged, and the electron is released from the charged domain boundary. A highly oriented film can satisfy this condition.

Examples of such satisfactory dielectric materials include $SrTiO_3$ (strontium titanate). $SrTiO_3$ is a perovskite compound, and when a stimulus such as an electric field, a magnetic field, or a light is applied thereto, the phase transition or domain boundary vibration is induced due to a cooperative phenomenon of an electric dipole, a magnetic dipole, a lattice vibration, etc., whereby the electrical characteristic is greatly changed. $SrTiO_3$ has a crystal structure with the highest symmetry at room temperature among perovskite compounds, and it generally does not have ferroelectricity, and thus does not have a domain boundary. However, $SrTiO_3$ can have the ferroelectricity and domain boundary in the state of a thin film due to mismatching to the crystal lattice constant or thermal expansion coefficient of a substrate (see, O. Tikhomirov et al., *Phys. Rev. Lett.*, 89, 2002, 147601, etc.) Though this domain boundary can be displaced by applying an electric field, the displacement generally requires an extremely high electric field. However, when the electron-attracting gas such as the oxygen gas is adsorbed around the domain boundary, the dielectric material is self-polarized, a large shearing stress is generated between crystalline planes, and thereby the energy barrier against the displacement of the domain boundary can be lowered.

For the purpose of lowering the resistance of $SrTiO_3$, thereby reducing the load of the detection current on an amplifier circuit, $Sr^{2+}$ may be partly substituted by an ion with a higher atomic valence such as a rare earth ion (e.g. $La^{3+}$, $Pr^{3+}$), and $Ti^{4+}$ may be partly substituted by an ion with a higher atomic valence (e.g. $Nb^{5+}$, $Ta^{5+}$). These substituents can increase the electron density in a shallow trap of $SrTiO_3$, and thus can lower the resistance. When the substitution rate is too high, the original dielectric characteristic of $SrTiO_3$ is deteriorated while a semiconductor characteristic is increased, and the detection properties are deteriorated. Thus, the substitution rate is preferably 0.1% or less. For the purpose of increasing the transient response current, $Sr^{2+}$ may be partly substituted by an ion with a lower atomic valence such as an alkali ion (e.g. $Na^+$, $K^+$), and $Ti^{4+}$ may be partly substituted by an ion with a lower atomic valence (e.g. $Cr^{3+}$, $Mn^{3+}$). These substituents can increase the density of electrons released due to displacement of a deep domain boundary in $SrTiO_3$, and thus can increase the transient current. When the substitution rate is too high, the domain boundary is hardly displaced, the original dielectric characteristic of $SrTiO_3$ is deteriorated, and the detection properties are deteriorated. Thus, the substitution rate is preferably 0.1% or less.

Figure 3:
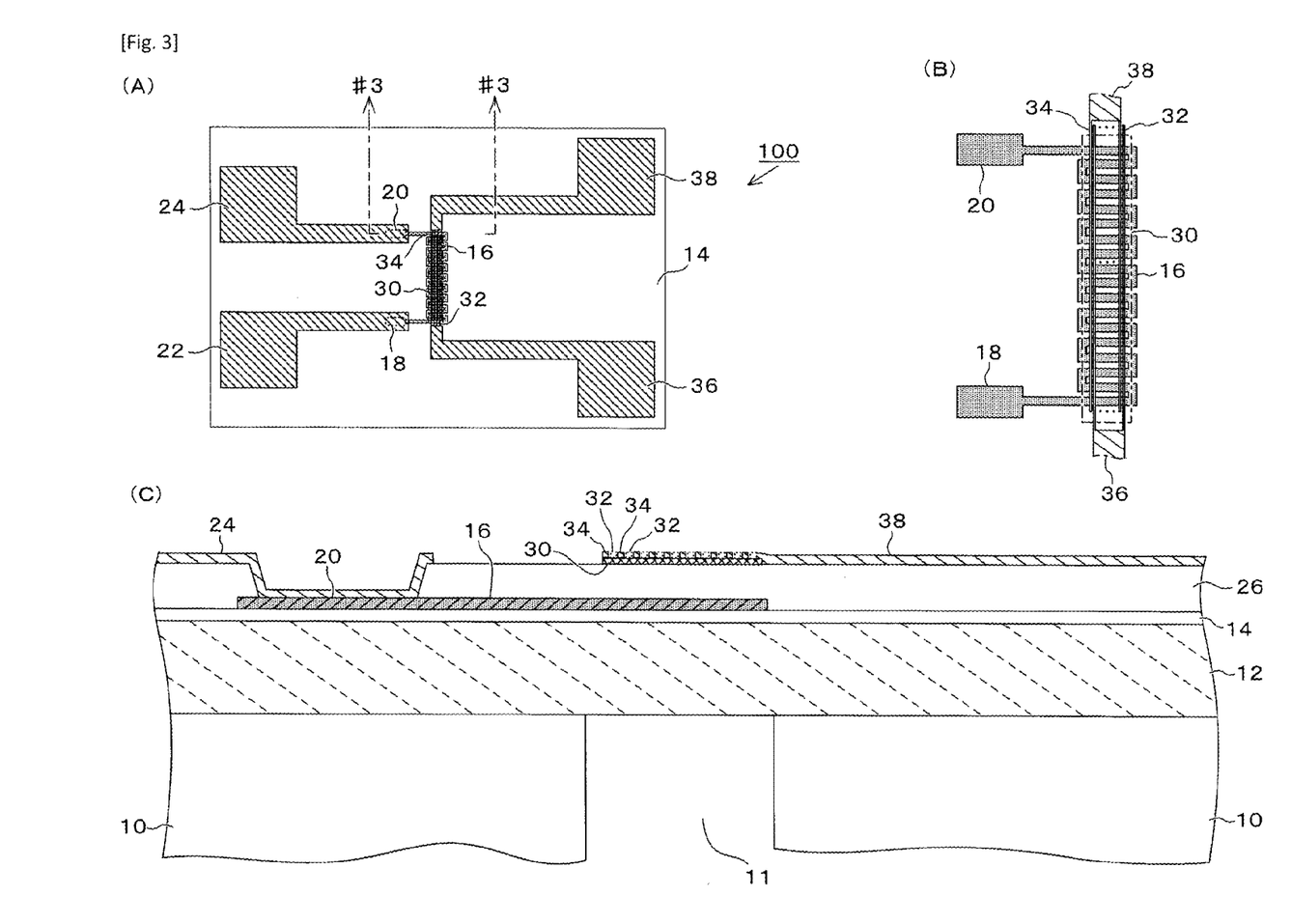
FIG. 3A is a plan view showing a gas sensor according to an example of the invention.
FIG. 3B is an enlarged view showing a main component of the gas sensor.
FIG. 3C is a cross-sectional view taken along the line #3-#3 of FIG. 3A observed in the direction of the arrows.
Figure 4:
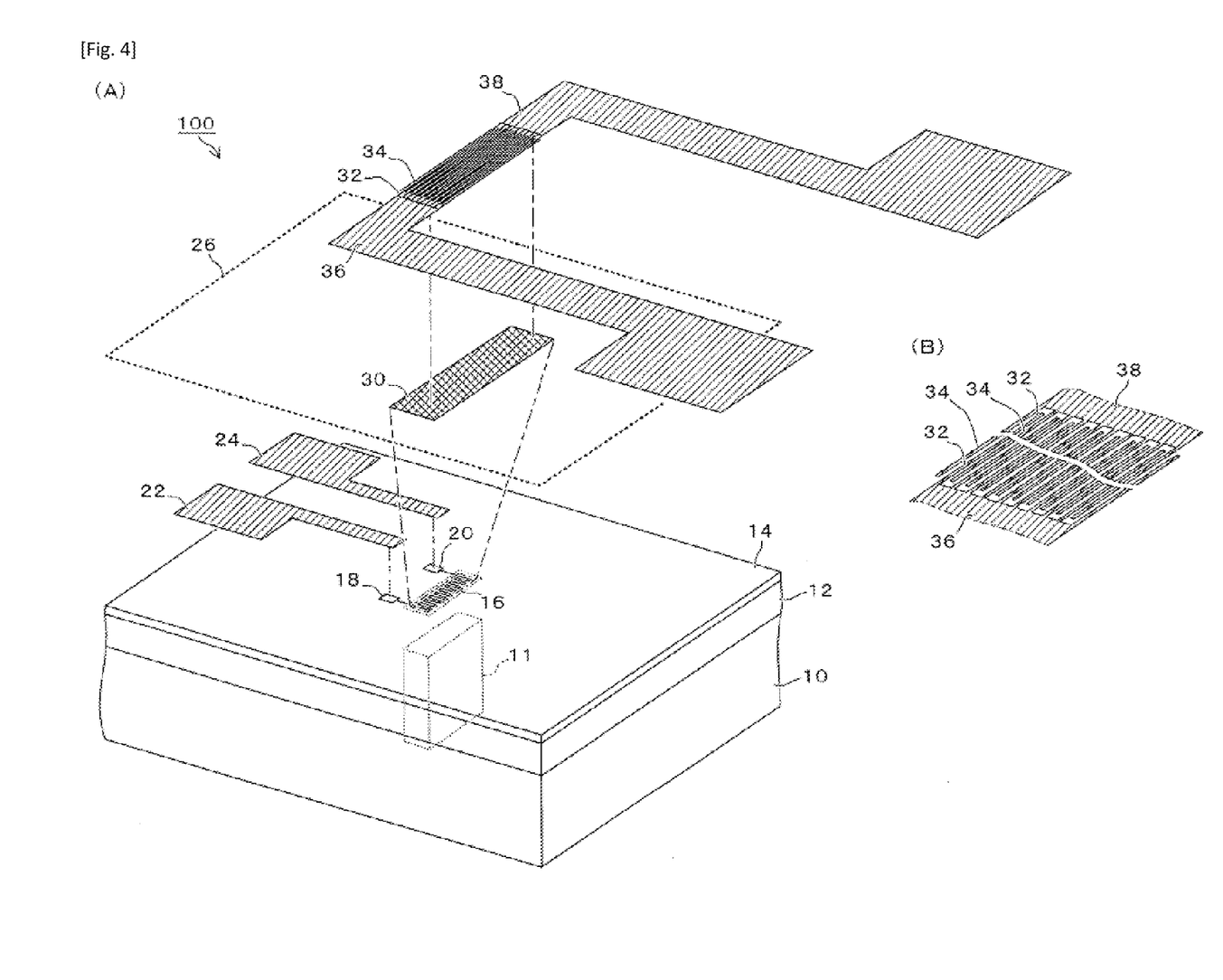
FIG. 4A is a perspective exploded view showing the main component.
FIG. 4B is an enlarged view showing an interdigitated electrode unit.

The structure of a gas sensor according to this example will be described below with reference to FIGS. 3A to 3C and 4A to 4B. FIG. 3A is a plan view showing the gas sensor, FIG. 3B is an enlarged view showing a main component of the gas sensor, and FIG. 3C is a cross-sectional view taken along the line #3-#3 of FIG. 3A observed in the direction of the arrows. FIG. 4A is a perspective exploded view showing the main component, and FIG. 4B is an enlarged view showing an interdigitated electrode unit. For example, as shown in the drawings, an $SiO_2$ layer 12 having a thickness of approximately 1,000 nm is formed on an Si substrate 10 by thermal oxidation, and an $Si_3N_4$ layer 14 having a thickness of 100 nm is formed thereon by thermal CVD. The $Si_3N_4$ layer 14 may be optionally formed if necessary.

Then, a heater 16 having a continuous meander line pattern due to a polycrystalline Si and extension portions 18, 20 thereof are formed to have a thickness of 100 nm by thermal CVD. Extension electrodes 22, 24 composed of a 200-nm-thick Au layer and a 10-nm-thick Ti layer, which extend from the extension portions 18, 20 outward, are formed by sputtering and liftoff, etc. An $SiO_2$ layer 26 having a thickness of approximately 250 nm (typically 200 nm to 300 nm) is formed on the heater 16 by thermal CVD and CMP.

A dielectric thin film 30 composed of a 10-nm-thick Ti layer and a 50-nm-thick $SrTiO_3$ layer is formed by sputtering and dry etching on the heater 16 with the $SiO_2$ layer 26 in-between. In an embodiment, the thickness of the dielectric thin film may be 2 nm to 200 nm. In an embodiment, the length and width of the dielectric thin film may be 0.1 mm to 1.0 mm, and 0.01 mm to 0.1 mm, respectively. Interdigitated electrodes 32, 34 are alternately formed on the dielectric thin film 30. The interdigitated electrodes are comb-like shaped each including a base portion and extension portions extending from the base portion. The number of the extension portions may be 5 to 50, the width of the extension portion may be 0.2 μm to 20 μm, and the distance between the extension portions next to each other may be 0.2 μm to 20 μm in an embodiment. The interdigitated electrodes 32, 34 are connected to extension electrodes 36, 38 respectively. The interdigitated electrodes 32, 34 and the extension electrodes 36, 38 are each composed of a 200-nm-thick Au layer and a 10-nm-thick Ti layer and formed by sputtering and liftoff, etc.

A space 11 is formed in the Si substrate 10 below the heater 16. The space 11 is formed in order to effectively transfer heat generated by the heater 16 to the dielectric thin film 30.

Figure 5:
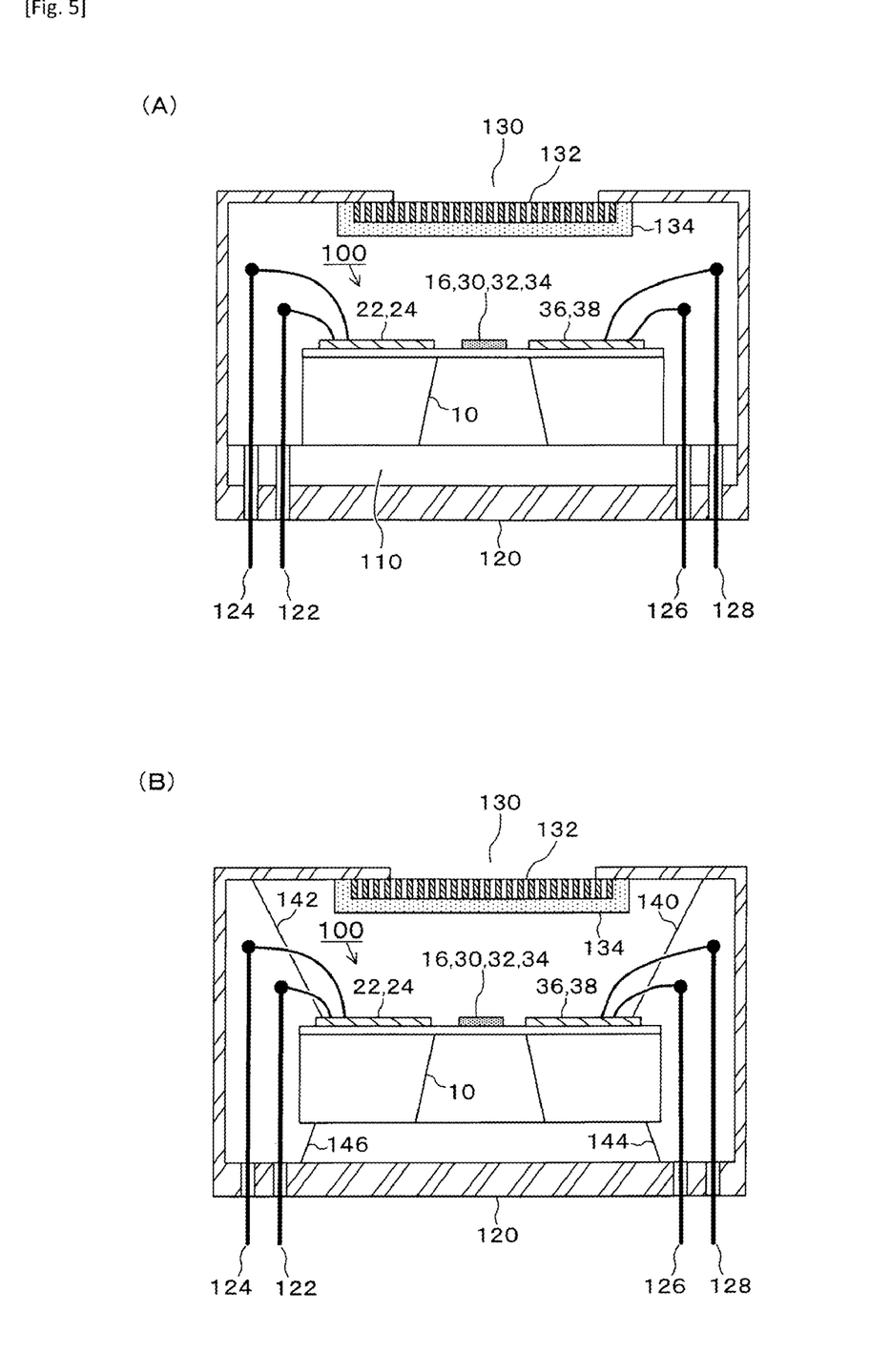
FIGS. 5A and 5B are views each showing an example of a package containing the gas sensor.

An example of a package containing the gas sensor 100 having the above structure is shown in FIG. 5A. In a stainless case 120, the gas sensor 100 is placed on a heat insulation glass substrate 110 for preventing heat generated by the heater 16 from leaking to the outside. The extension electrodes 22, 24 of the gas sensor 100 are connected to terminals 122, 124 respectively, and the extension electrodes 36, 38 are connected to terminals 126, 128 respectively. A gas introducing window or opening 130 is formed on the upper surface of the stainless case 120. A protective stainless mesh 132 is formed in the window 130, and a gas permeable membrane 134 of a porous polymer film is formed on the stainless mesh 132. The analyte gas can pass through the gas permeable membrane 134, but dust and water cannot pass therethrough. Another example of a package, in which the gas sensor 100 is supported by wires 140, 142, 144, 146 without the glass substrate 110, is shown in FIG. 5B.

A gas concentration determination procedure using the gas sensor of this example will be described below with reference to FIGS. 6A to 6D. The determination procedure contains a measuring mode and a refreshing mode. Further, the refreshing mode contains two stages of a heating mode and a backgating mode. The modes are described in detail below.

Figure 6:
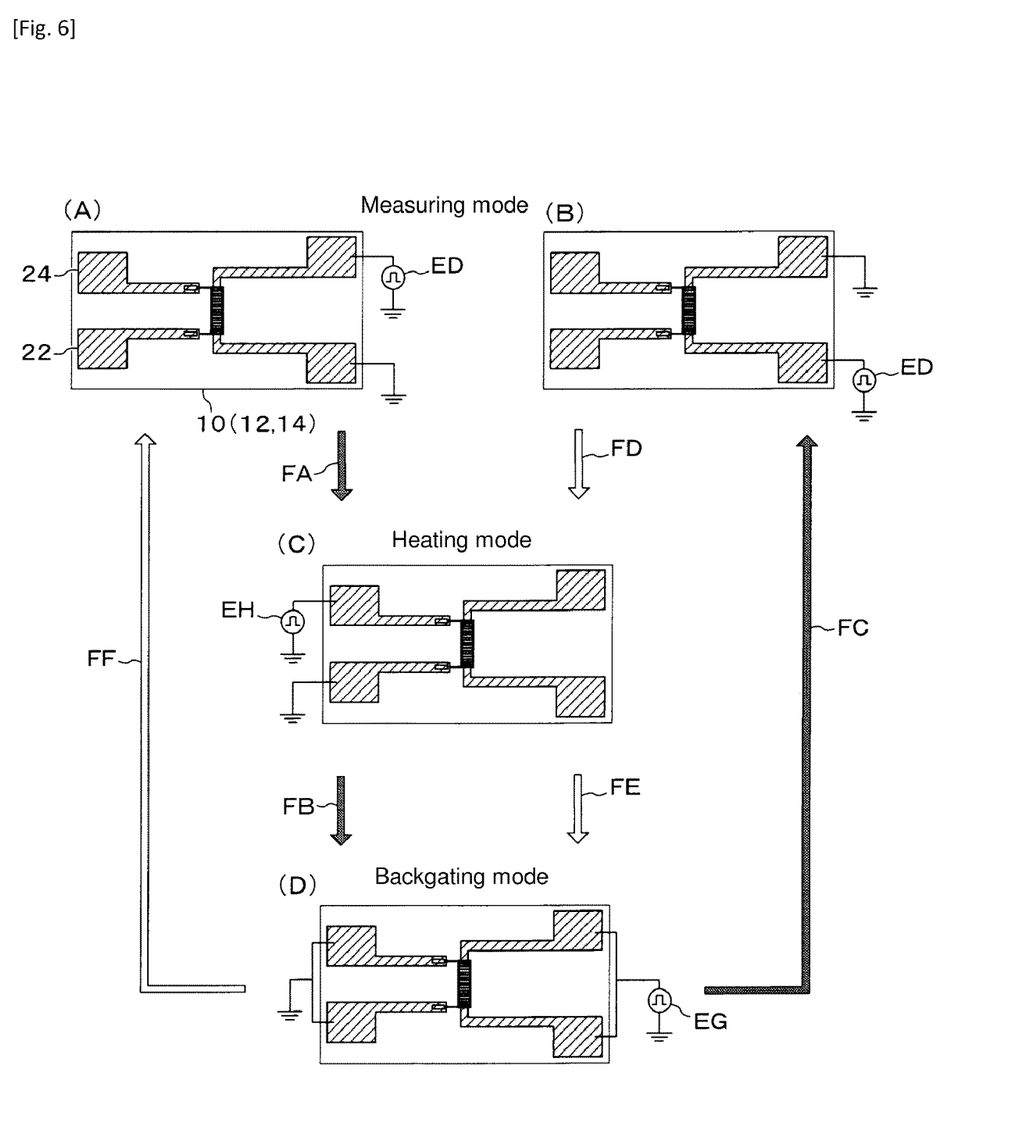
FIGS. 6A to 6D are views showing a measurement procedure using the gas sensor.

(1) Heating mode: As shown in FIG. 6C, a power source EH is connected to the extension electrodes 22, 24 to apply electricity to the heater 16. Then, the heater 16 generates heat, and the dielectric thin film 30 is heated, so that the self-polarization of the dielectric thin film 30 is eliminated.

(2) Backgating mode: As shown in FIG. 6D, a reverse electric field is applied to the dielectric thin film 30. The reverse electric field is opposite to an internal electric field generated in the film when the gaseous molecule is adsorbed.

After the previous measurement, the dielectric thin film 30 is in the gas adsorption/discharge equilibrium state. By applying the reverse electric field, a gaseous molecule is forcibly released from a surface of the dielectric thin film 30 temporarily, whereby the surface is refreshed.

(3) Measuring mode: As shown in FIG. 6A or 6B, a measurement voltage is applied to the interdigitated electrodes 32 and 34, and a transient response is detected by pulse resistivity measurement while gaseous molecules are gradually adsorbed to the refreshed surface of the dielectric thin film 30. The first measurement is carried out after the first refreshing, and the second measurement is carried out after the second refreshing. A voltage used in the second measurement has a polarity opposite to that of a voltage used in the first measurement. For example, in a case where the first measurement is carried out in the state shown in FIG. 6A, the refreshing is carried out in the state shown in FIGS. 6C and 6D, and then the second measurement is carried out in the state shown in FIG. 6B (see arrows FA, FB, and FC). In contrast, in a case where the first measurement is carried out in the state shown in FIG. 6B, the refreshing is carried out in the state shown in FIGS. 6C and 6D, and then the second measurement is carried out in the state shown in FIG. 6A (see arrows FD, FE, and FF).

In an embodiment, the voltage applied to the dielectric thin film in the heating mode may be 5 V to 15 V. In an embodiment, the voltage applied to the dielectric thin film in the backgating mode may be 5 V to 15 V. In an embodiment, the electric field applied to the dielectric thin film in the measuring mode may be 0.1 V/μm to 10 V/μm. The transient current in the measuring mode may be on the order of $\mu A$ to $10^2$ $\mu A$.

As described above, in the case of detecting a low concentration gas which is an object of at least one embodiment of the invention, the surface of the dielectric thin film 30 is covered with the gaseous molecules over a long time. Thus, the resistance of the dielectric thin film 30 slowly reaches the steady-state value in a long time. Therefore, the preferable gas concentration measurement can be carried out over a satisfactory long time.

OTHER EXAMPLE

The invention is not limited to the above example, and various changes and modifications may be made therein without departing from the scope of the invention. For example, the skilled artisan could modify the above example as follows.

(1) Though the oxygen gas is used as the concentration measurement analyte in the above example, the analyte may be any electron-attracting gas. A plurality of the above sensor structures may be arranged on one substrate to produce a sensor array for detecting a plurality of gases. In this case, the above gas permeable membrane 134 used in the package is such that the measurement analyte gases can pass therethrough.

(2) The material, thickness, shape, etc. of each component described in the above example are to be considered in all respects as illustrative and not restrictive, and may be changed as long as the same effects can be obtained.

The gas sensor and the gas detection method of the present invention are capable of detecting an extremely small amount of a gas, and thereby are useful in various fields of semiconductor manufacturing, food production/manufacturing/distribution, medical care, etc.

The present invention includes the above mentioned embodiments and other various embodiments including the following:

1) A gas sensor comprising a dielectric thin film and a voltage applying unit, wherein
the dielectric thin film has a domain boundary formed between domains having different polarization directions in a crystal,
the voltage applying unit applies a voltage for measuring an electric resistance change based on adsorption of a gaseous molecule to the dielectric thin film, and
a transient current generated due to displacement of the domain boundary is measured to determine the concentration of the adsorbed gaseous molecule.

2) A gas sensor according to 1), wherein the dielectric thin film comprises a polycrystal containing $SrTiO_3$ as a main component.

3) A gas sensor according to 1) or 2), further comprising a heating unit for heating the dielectric thin film.

4) A gas sensor comprising
an insulative substrate,
a heating unit formed on the insulative substrate, capable of generating heat on its surface under an applied voltage,
a dielectric thin film formed on the heating unit on the insulative substrate with an insulative film in-between, and
an electrode unit formed on the dielectric thin film, having electrodes facing each other at a predetermined distance, capable of applying a voltage for measuring a transient current corresponding to a gas concentration.

5) A gas sensor according to 4), wherein the dielectric thin film comprises a polycrystal containing $SrTiO_3$ as a main component.

6) A gas sensor according to 4) or 5), wherein the dielectric thin film is heated by the heating unit for a predetermined time before determination of the gas concentration, whereby a gaseous molecule adsorbed to the dielectric thin film is released to refresh the dielectric thin film.

7) A gas sensor according to 4), wherein the electrode unit has interdigitated portions facing each other on the dielectric thin film, and extension portions extend from the interdigitated portions respectively.

8) A method for detecting a gas, comprising the steps of
applying a voltage for measuring to a dielectric thin film, which has a domain boundary formed between domains having different polarization directions in a crystal, and
measuring a transient current generated due to displacement of the domain boundary corresponding to the concentration of a gaseous molecule adsorbed to the dielectric thin film, thereby determining the concentration.

9) A method according to 8), wherein the dielectric thin film comprises a polycrystal containing $SrTiO_3$ as a main component.

10) A method for detecting a gas using a gas sensor according to 3), comprising
a refreshing mode of releasing a gaseous molecule adsorbed to the dielectric thin film to refresh the dielectric thin film, and
a measuring mode of detecting a transient current, which is generated under an applied voltage when a gaseous molecule is adsorbed to the dielectric thin film refreshed in the refreshing mode.

11) A method according to 10), wherein the refreshing mode comprises
a heating mode of heating the dielectric thin film using the heating unit, and
a backgating mode of applying a reverse electric field to the dielectric thin film heated in the heating mode, the reverse electric field being opposite to an electric field generated in the dielectric substance when the gaseous molecule is adsorbed.

The present application claims priority to Japanese Patent Application No. 2007-256345, filed Sep. 28, 2007, and No. 2008-192882, filed Jul. 25, 2008, the disclosure of each of which is incorporated herein by reference in its entirety.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A gas sensor comprising:
a dielectric thin film composed of a crystal having domain boundaries formed between immediately adjacent domains having different polarization directions, and
a voltage applying unit for applying a voltage to the dielectric thin film for measuring a transient current generated when a gaseous molecule is absorbed to the dielectric thin film,
wherein the transient current is generated due to shifting of the domain boundaries and is measured to determine the concentration of the adsorbed gaseous molecule.

2. A gas sensor comprising:
a dielectric thin film composed of a crystal having domain boundaries formed between immediately adjacent domains having different polarization directions, and
a voltage applying unit for applying a voltage to the dielectric thin film for measuring a transient current generated when a gaseous molecule is absorbed to the dielectric thin film,
wherein the crystal of the dielectric thin film contains domains having a polarization direction of other than 180°.

3. The gas sensor according to claim 2, wherein the dielectric thin film comprises a polycrystal containing $SrTiO_3$ as a main component.

4. The gas sensor according to claim 2, further comprising a heating unit for heating the dielectric thin film.

5. A gas sensor comprising:
a dielectric thin film composed of a crystal having domain boundaries formed between immediately adjacent domains having different polarization directions,
a voltage applying unit for applying a voltage to the dielectric thin film for measuring a transient current generated when a gaseous molecule is absorbed to the dielectric thin film,
a heating unit for heating the dielectric thin film, and
an insulative substrate on which the heating unit is formed, said heating unit being capable of generating heat on its surface under an applied voltage, wherein
the dielectric thin film is formed on the heating unit via an insulative film interposed between the dielectric thin film and the heating unit, and
the voltage applying unit comprises an electrode unit formed on the dielectric thin film, having two electrodes facing each other at a given distance, capable of applying a voltage for measuring a transient current corresponding to a gas concentration.

6. The gas sensor according to claim 5, wherein the dielectric thin film comprises a polycrystal containing $SrTiO_3$ as a main component.

7. The gas sensor according to claim 5, wherein the dielectric thin film is refreshable by releasing a gaseous molecule adsorbed to the dielectric thin film when the dielectric thin film is heated by the heating unit for a given time before determination of the gas concentration.

8. The gas sensor according to claim 5, wherein the electrodes have base portions facing each other as a give distance on the dielectric thin film, and extension portions extending from the respective base portions toward each other.

9. A method for detecting a gas using the gas sensor of claim 2, comprising:
applying a voltage to the dielectric thin film via the voltage applying unit of the gas sensor, and
measuring a transient current generated due to displacement of the domain boundary corresponding to the concentration of a gaseous molecule adsorbed to the dielectric thin film, thereby determining the concentration.

10. The method according to claim 9, wherein the dielectric thin film comprises a polycrystal containing $SrTiO_3$ as a main component.

11. The method according to claim 9, further comprising:
prior to the step of measuring a transient current, refreshing the dielectric thin film by releasing a gaseous molecule adsorbed to the dielectric thin film.

12. The method according to claim 11, wherein the step of refreshing comprises
heating the dielectric thin film using the heating unit, and
applying a reverse electric field to the dielectric thin film heated in the heating step, the reverse electric field being opposite to an electric field generated within the dielectric thin film when the gaseous molecule is adsorbed.

13. The method according to claim 9, wherein the gas to be detected is an electron-attracting gas.

* * * * *